US012168112B2

(12) United States Patent
Kemper et al.

(10) Patent No.: US 12,168,112 B2
(45) Date of Patent: Dec. 17, 2024

(54) SYSTEMS AND METHODS FOR MONITORING HYGIENE PRACTICES ASSOCIATED WITH POWERED CONTRAST INJECTIONS

(71) Applicant: BAYER HEALTHCARE LLC, Whippany, NJ (US)

(72) Inventors: Corey Kemper, Pittsburgh, PA (US); John Volkar, Valencia, PA (US); Christopher Lazzara, Cranberry Township, PA (US); Matthias Burg, Berlin (DE)

(73) Assignee: BAYER HEALTHCARE LLC, Whippany, NJ (US)

( * ) Notice: Subject to any disclaimer, the term of this patent is extended or adjusted under 35 U.S.C. 154(b) by 1114 days.

(21) Appl. No.: 17/044,192

(22) PCT Filed: Apr. 9, 2019

(86) PCT No.: PCT/US2019/026659
§ 371 (c)(1),
(2) Date: Sep. 30, 2020

(87) PCT Pub. No.: WO2019/199885
PCT Pub. Date: Oct. 17, 2019

(65) Prior Publication Data
US 2021/0046240 A1 Feb. 18, 2021

Related U.S. Application Data

(60) Provisional application No. 62/655,374, filed on Apr. 10, 2018.

(51) Int. Cl.
*A61M 5/00* (2006.01)
*G16H 20/17* (2018.01)

(52) U.S. Cl.
CPC ............ *A61M 5/007* (2013.01); *G16H 20/17* (2018.01); *A61M 2205/273* (2013.01); *A61M 2205/583* (2013.01)

(58) Field of Classification Search
CPC ............................... A61M 5/007; G16H 20/17
See application file for complete search history.

(56) References Cited

U.S. PATENT DOCUMENTS

2008/0213872 A1\* 9/2008 Regan .................... G01N 35/08
422/255
2014/0224829 A1\* 8/2014 Capone ............... B05B 11/1015
222/23

(Continued)

FOREIGN PATENT DOCUMENTS

| WO | 2014144651 A2 | 9/2014 |
| WO | 2015106107 A1 | 7/2015 |
| WO | 2018144369 A1 | 8/2018 |

OTHER PUBLICATIONS

"International Preliminary Report on Patentability from PCT/US2019026659", Oct. 22, 2020.

(Continued)

*Primary Examiner* — Dung T Ulsh
(74) *Attorney, Agent, or Firm* — James R. Stevenson; Joseph L. Kent

(57) ABSTRACT

A fluid injector system for use in administering to a patient a fluid in an injection protocol in connection with a diagnostic imaging procedure includes at least one display and a control device. The control device is programmed to determine, for each of the injection protocols performed by the fluid injector system, a component status for the at least one disposable component. The component status indicates whether use of the at least one disposable component was compliant with instructions for use applicable to the at least one disposable component. The control device is further (Continued)

programmed to enable the at least one display to display a compliance report. The compliance report includes one or more visual indicators providing visual feedback about compliance with the instructions for use based on the component status determined for each of the injection protocols performed using the fluid injector system.

14 Claims, 10 Drawing Sheets

(56) References Cited

U.S. PATENT DOCUMENTS

| | | | |
|---|---|---|---|
| 2014/0276379 A1* | 9/2014 | Uram | A61M 5/007 29/428 |
| 2017/0258982 A1 | 9/2017 | Kemper | |

OTHER PUBLICATIONS

Bayer., "MRXperion OpManual—3038591 Rev H Feb. 13, 2018", Feb. 13, 2018.
"Mark 7 Arterion Injection System Operation Manual, Rev. Q", Jan. 21, 2017.

* cited by examiner

SYSTEMS AND METHODS FOR MONITORING HYGIENE PRACTICES ASSOCIATED WITH POWERED CONTRAST INJECTIONS

CROSS-REFERENCE TO RELATED APPLICATION

This application is a U.S. national phase application under 35 U.S.C. § 371 of PCT International Application No. PCT/US2019/026659, filed Apr. 9, 2019 and claims priority to U.S. Provisional Patent Application No. 62/655,374, filed Apr. 10, 2018, the disclosures of which are hereby incorporated by reference in their entirety.

BACKGROUND

Field of the Invention

The present disclosure is directed to a fluid injector system and methods that provide feedback about use of the fluid injector system and, in particular, to systems and methods for providing visual feedback regarding compliance with instructions for use and hygiene practices for disposables of the fluid injector system.

Description of Related Art

In many medical diagnostic and therapeutic procedures, a medical practitioner, such as a medical technologist, injects a patient with one or more medical fluids. In recent years, a number of medical fluid delivery systems for pressurized injection of fluids, such as a contrast media (often referred to simply as "contrast"), flushing agent(s), such as saline, and other medical fluids, have been developed for use in procedures such as angiography, computed tomography (CT), ultrasound, magnetic resonance imaging (MRI), positron emission tomography (PET) and various other imaging procedures. In general, these medical fluid delivery systems, such as powered fluid injectors, are designed to deliver such fluids via one or more injection protocols. An injection protocol can include one or more injections, each comprising one or more phases to enhance regions of interest in a patient's body during diagnostic imaging. Examples of powered fluid injectors that are capable of delivering such fluids via user-programmable multi-phase injection protocols include the MEDRAD® Stellant CT Injection System, the MEDRAD® Stellant FLEX CT Injection System, the MEDRAD® MRXperion MR Injection System and the MEDRAD® Centargo CT Injection System, all of which produced by Bayer HealthCare LLC.

Many fluid injection systems are designed to be used with single-use disposable components but others are designed to be used with both multi-use and single-use disposable components. As an example of the former, the MEDRAD® Stellant CT Injection System is designed to be used with one or two single-use disposable syringes through which fluid pressurized via an equal number of drive members is delivered via a single-use disposable set (SUDS), also referred to as a single-use fluid path set or patient line, into the patient. The patient line has a proximal end that is designed to connect to, or at least be in fluid communication with, the syringe(s) and a distal end intended for connection to a vascular access device that is to be inserted into a blood vessel, such as a vein, of the patient. As an example of the latter, the MEDRAD® Centargo CT Injection System is designed to be used with a multi-use disposable set (MUDS) from which pressurized fluid(s) flow through a single-use disposable set (SUDS) into the patient. The MUDS can be used for multiple patients and/or for multiple injection protocols. The MUDS can include, for example, at least one syringe designed to be connected to the appropriate fluid source(s) and tubing or connectors for establishing fluid communication between the syringe(s) and the patient line or SUDS. The MUDS can be used for a number of patients over an in-use time or usable life. For example, instructions for use of the MUDS may indicate that it should be replaced every 4 hours, 12 hours, or daily. The instructions for use may also indicate that the need for replacement could be based on patient count. For example, the instructions for use could state that the MUDS should be replaced after being used for a predetermined number of injection protocols or patients, such as 5 or 10 injection protocols or patients. In both types of injection system, the SUDS is generally intended to be replaced for each new patient and/or for each new injection protocol Disposables, such as the MUDS, are tested to their expiration or in-use time (e.g., from 4 hours to one day). Use beyond expiration can lead to disposable failure, environmental contamination, and other potential risks to patients. Use beyond expiration can also cause additional stress on the electromechanical hardware of the fluid injector system. Re-use of the SUDS for multiple patients can lead to cross-contamination between patients, putting patients at risk of blood-borne infections.

In order to avoid use of the MUDS beyond expiration and/or use of the SUDS for multiple patients, fluid injector systems can include, for example, expiration timers, audio or visual alerts, and labeling to notify medical practitioners that disposable components need to be changed. Some injectors can also include sensors and software that monitor disposables to prevent off-label use. For example, a barcode, QR code, or RFID tag can be affixed to every disposable. The code or RFID tag can be manually or automatically scanned before each injection to determine information about the disposable component being used for the injection. For example, such tracking can allow the system to track which SUDS is used for an injection and to ensure that the SUDS is not re-used.

Disposable components can also be designed to prevent re-use (e.g., for single-use connectors or SUDS) and to prevent prolonged use beyond expiration (e.g., for multi-use connectors or MUDS). For example, some single-use components include pieces designed to break when mounted to the injector and/or following an injection to render the component unusable to perform a second injection.

In some cases, product packaging of the disposables is designed to encourage medical practitioners to use disposable components according to usage instructions. For example, a daily supply of patient lines (e.g., SUDS) can be packaged together with one MUDS. Such packaging can encourage the user (e.g., the medical technologist) to use all of the patient lines or SUDS during the day. Once all of the SUDS have been used, which should take about one day, the technologist may be instructed to discard the MUDS, open a new package, and install the MUDS from the newly opened package to the fluid injector. In this way, the product packaging both encourages the user to replace the SUDS following each injection (e.g., to ensure that all of the SUDS in the package are used in one day) and to replace the MUDS daily, once all of the SUDS in the package have been used.

As will be appreciated by those skilled in the art, the modifications to the fluid injector or disposables to encourage compliance and for avoiding incorrect use of disposable components often require technologists to perform additional steps (e.g., scanning tags or labels) to confirm that use of the disposable is in accordance with the instructions for use. Also, such modifications can add complexity and/or additional costs for fluid injector systems and disposable components. For example, molding breakable pieces to the SUDS to prevent reuse may increase manufacturing costs or make the SUDS more likely to brake before or during use.

SUMMARY

In view of the difficulties in informing users about incorrect use of disposable components, there is a need for improved feedback systems to encourage users to use and replace disposables in compliance with usage instructions. The systems and methods of the present disclosure are intended to provide such feedback to users to encourage compliance and safe, hygienic practices. In particular, the systems, computer program products, and methods disclosed herein are related to visual feedback systems that display to the users indicators about compliance with usage instructions over the course of a predetermined period (e.g., days, weeks, or months). The visual feedback systems, computer program products, and methods disclosed herein generally do not otherwise interfere with operation of the fluid injector system or treatment of patients.

According to an aspect of the disclosure, a fluid injector system for use in administering to a patient at least one fluid in an injection protocol in connection with a diagnostic imaging procedure includes at least one display and a control device operably associated with at least one drive component for use in pressurizing the at least one fluid through at least one disposable component into a patient. The control device includes at least one processor programmed or configured to enable programming of an injection protocol including one or more injections, each of the injections having one or more phases according to which the at least one drive component pressurizes the least one fluid through the at least one disposable component into the patient so as to effect enhancement of at least one region of interest thereof over a scan duration of the diagnostic imaging procedure. The control device is further programmed or configured to determine, for each of the injection protocols performed by the fluid injector system, a component status for the at least one disposable component. The component status indicates whether use of the at least one disposable component was compliant with instructions for use applicable to the at least one disposable component. The control device is further programmed or configured to enable the at least one display to display a compliance report. The compliance report includes one or more visual indicators providing visual feedback about compliance with the instructions for use based on the component status determined for each of the injection protocols performed using the fluid injector system.

According to another aspect of the disclosure, a computer program product provides visual feedback for a plurality of injection protocols performed by a fluid injector system. The fluid injector system is designed for use in pressurizing at least one fluid through at least one disposable component into a patient in connection with a diagnostic imaging procedure. The computer program product includes non-transitory computer readable media comprising one or more instructions that, when executed by at least one processor, cause the at least one processor to determine, for each of the injection protocols, a component status for the at least one disposable component. The component status indicates whether use of the at least one disposable component was compliant with instructions for use applicable to the at least one disposable component. The one or more instructions also cause the at least one processor to cause at least one display to display a compliance report. The compliance report includes one or more visual indicators providing visual feedback about compliance with the instructions for use based on the component status determined for each of the injection protocols performed using the fluid injection system.

According to another aspect of the disclosure, a computer-implemented method is disclosed for providing visual feedback about a plurality of injection protocols performed by a fluid injector system. The fluid injector system is designed for use in pressurizing at least one fluid through at least one disposable component into a patient in connection with a diagnostic imaging procedure is provided. The method includes determining, for each of the injection protocols performed by the fluid injector system, a component status for the at least one disposable component. The component status indicates whether use of the at least one disposable component was compliant with instructions for use applicable to the at least one disposable component. The method also includes causing at least one display to display a compliance report. The compliance report includes one or more visual indicators providing visual feedback about compliance with the instructions for use based on the component status determined for each of the injection protocols performed using the fluid injection system.

In accordance with some examples or aspects, the disclosure of the present application may be characterized by one or more of the following numbered clauses:

Clause 1: A fluid injector system for use in administering to a patient at least one fluid in an injection protocol in connection with a diagnostic imaging procedure, the fluid injector system including at least one display, the fluid injector system comprising: a control device operably associated with at least one drive component for use in pressurizing the at least one fluid through at least one disposable component into a patient; and the control device including at least one processor programmed or configured to enable programming of an injection protocol comprising one or more injections, each of the injections comprising one or more phases according to which the at least one drive component pressurizes the least one fluid through the at least one disposable component into the patient so as to effect enhancement of at least one region of interest thereof over a scan duration of the diagnostic imaging procedure; wherein the control device is further programmed or configured to: determine, for each of the injection protocols performed by the fluid injector system, a component status for the at least one disposable component wherein the component status indicates whether use of the at least one disposable component was compliant with instructions for use applicable to the at least one disposable component; and enable the at least one display to display a compliance report, the compliance report comprising one or more visual indicators providing visual feedback about compliance with the instructions for use based on the component status determined for each of the injection protocols performed using the fluid injector system.

Clause 2: The fluid injector system of clause 1, wherein the component status indicates whether the use of the at least one disposable component of the fluid injector system was compliant with the instructions for use applicable thereto or was not compliant with the instructions for use applicable thereto.

Clause 3: The fluid injector system of clause 1 or clause 2, wherein the control device is further programmed or configured to determine an occurrence time for each of the injection protocols.

Clause 4: The fluid injector system of clause 3, wherein, for each of the injection protocols, the control device is further programmed or configured to determine an installation time for the at least one disposable component used for the injection protocol.

Clause 5: The fluid injector system of clause 4, wherein, for each of the injection protocols, the determination of the component status is based on a comparison between the installation time for the at least one disposable component and the occurrence time for the injection protocol.

Clause 6: The fluid injector system of clause 4 or clause 5, wherein the component status indicates that use of the at least one disposable component was compliant with instructions for use applicable thereto when the occurrence time for the injection protocols is within a predetermined period from the installation time of the at least one disposable component.

Clause 7: The fluid injector system of any of clauses 4-6, further comprising at least one sensor configured to detect installation of the at least one disposable component into the fluid injector system.

Clause 8: The fluid injector system of clause 7, wherein the control device is further programmed or configured to determine the installation time of the at least one disposable component into the fluid injector system based on information received from the at least one sensor.

Clause 9: The fluid injector system of any of clauses 1-8, wherein the at least one disposable component comprises at least one of a multi-use component of the fluid injector system or a single-use component of the fluid injector system.

Clause 10: The fluid injector system of any of clauses 1-9, wherein the component status for each injection protocol comprises a first status for a multi-use component of the fluid injector system and a second status for a single-use component of the fluid injector system.

Clause 11: The fluid injector system of clause 10, wherein the multi-use component comprises at least one syringe configured to be used by multiple patients, and wherein the single-use component comprises a patient line configured to be placed in fluid communication with the at one syringe and used by a single patient.

Clause 12: The fluid injector system of clause 11, wherein the instructions for use applicable to the multi-use component permit the multi-use component to be used for at least one of a predetermined period of time or a predetermined number of injection protocols.

Clause 13: The system of any of clauses 1-12, wherein, for each of the injection protocols performed by the fluid injector system, the control device is further programmed or configured to associate the component status determined for the at least one disposable component with a time interval of a plurality of time intervals.

Clause 14: The system of clause 13, wherein the compliance report comprises at least one of the one or more visual indicators for each time interval of the plurality of time intervals, the at least one visual indicator for each time interval being based on the component status determined for the at least one disposable component associated with the time interval of the plurality of time intervals.

Clause 15: The fluid injector system of clause 14, wherein the compliance summary comprises a matrix comprising a space for each of the at least one of the one or more visual indicators for each time interval of the plurality of time intervals.

Clause 16: The fluid injector system of clause 14 or clause 15, wherein the at least one of the one or more visual indicators for each time interval of the plurality of intervals comprises a first appearance when each component status for the time interval indicates compliance with the instructions for use, and a second appearance when at least one of the component statuses for the interval indicates that use was not compliant with the instructions for use of the at least one disposable component.

Clause 17: The fluid injector system of any of clauses 14-16, wherein the compliance report further comprises at least one visual indicator for total compliance generated based on the determined component statuses for each of the plurality of time intervals.

Clause 18: The fluid injector system of clause 17, wherein the visual indicator for total compliance comprises a bar graph comprising a first bar indicating compliance and at least one second bar indicating non-compliance.

Clause 19: A computer program product for providing visual feedback for a plurality of injection protocols performed by a fluid injector system, the fluid injector system for use in pressurizing at least one fluid through at least one disposable component into a patient in connection with a diagnostic imaging procedure, the computer program product comprising non-transitory computer readable media comprising one or more instructions that, when executed by at least one processor, cause the at least one processor to: determine, for each of the injection protocols, a component status for the at least one disposable component, wherein the component status indicates whether use of the at least one disposable component was compliant with instructions for use applicable to the at least one disposable component; and cause at least one display to display a compliance report, the compliance report comprising one or more visual indicators providing visual feedback about compliance with the instructions for use based on the component status determined for each of the injection protocols performed using the fluid injection system.

Clause 20: The computer program product of clause 19, wherein the component status indicates whether use of at least one disposable component of the fluid injector system was compliant with the instructions of use applicable thereto or was not compliant with the instructions for use applicable thereto.

Clause 21: The computer program product of clause 19 or clause 20, wherein the instructions further cause the at least one processor to determine an occurrence time for each of the injection protocols.

Clause 22: The computer program product of clause 21, wherein, for each of the plurality of injection protocols, the instructions cause the at least one processor to determine an installation time for the at least one disposable component used for the injection protocol.

Clause 23: The computer program product of clause 22, wherein the instructions cause the at least one processor to determine the component status for each of the plurality of injection protocols based on a comparison between the installation time for the at least one disposable component and the occurrence time for the injection protocol.

Clause 24: The computer program product of clause 22 or clause 23, wherein the component status indicates that use of the at least one disposable component was compliant with instructions for use applicable thereto when the occurrence time for the injection protocols is within a predetermined period from the installation time of the at least one disposable component.

Clause 25: The computer program product of any of clauses 19-24, wherein the instructions further cause the at least one processor to associate the component status determined for the at least one disposable component with a time interval of a plurality of time intervals.

Clause 26: The computer program product of clause 25, wherein the compliance report comprises at least one of the one or more visual indicators for each time interval of the plurality of time intervals, the at least one visual indicator for each time interval being based on the component status determined for the at least one disposable component associated with the time interval of the plurality of time intervals.

Clause 27: A computer-implemented method for providing visual feedback about a plurality of injection protocols performed by a fluid injector system for use in pressurizing at least one fluid through at least one disposable component into a patient in connection with a diagnostic imaging procedure, the method comprising: determining, for each of the injection protocols performed by the fluid injector system, a component status for the at least one disposable component wherein the component status indicates whether use of the at least one disposable component was compliant with instructions for use applicable to the at least one disposable component; and causing at least one display to display a compliance report, the compliance report comprising one or more visual indicators providing visual feedback about compliance with the instructions for use based on the component status determined for each of the injection protocols performed using the fluid injection system.

DETAILED DESCRIPTION

Figure 1:
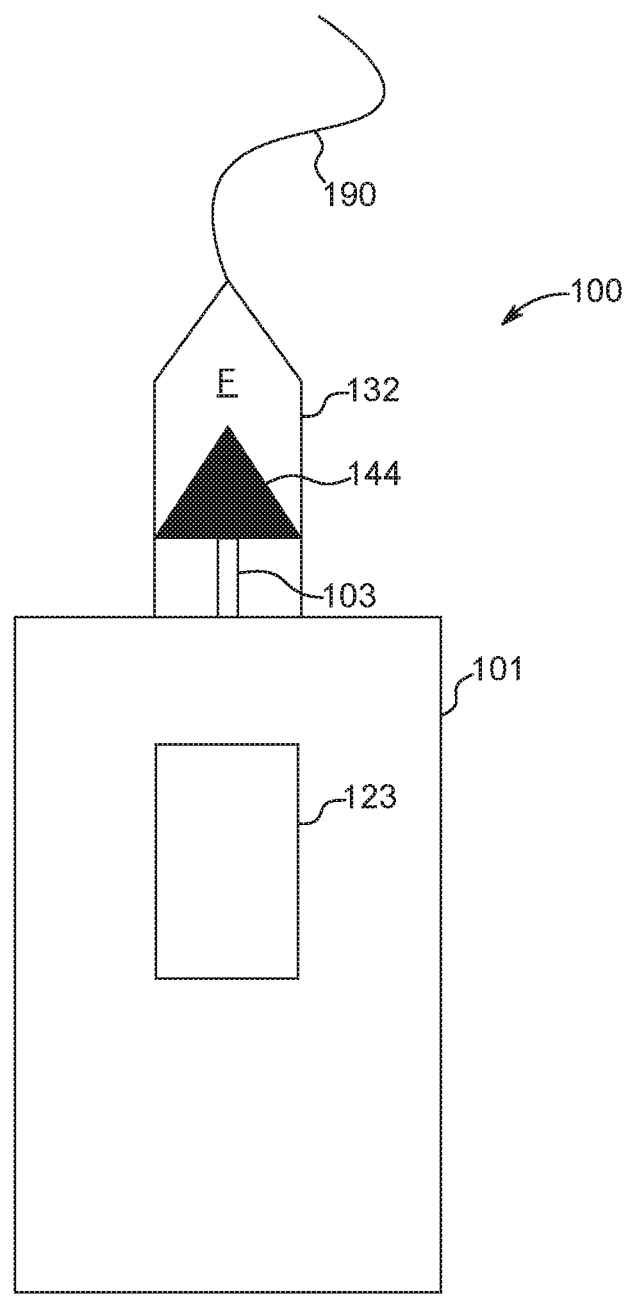
FIG. 1 is a schematic view of a powered fluid injector system in accordance with some examples or aspects of the present disclosure.

The illustrations generally show preferred and non-limiting examples or aspects of the systems and methods of the present disclosure. While the description presents various examples or aspects of the devices, it should not be interpreted in any way as limiting the disclosure. Furthermore, modifications, concepts, and applications of the disclosure's examples or aspects are to be interpreted by those skilled in the art as being encompassed by, but not limited to, the illustrations and descriptions herein.

The following description is provided to enable those skilled in the art to make and use the described examples or aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to an administration line, the term "proximal" refers to a portion of an administration line nearest to a powered fluid injector. When used in relation to an administration line, the term "distal" refers to a portion of an administration line nearest to an injection site on a patient. When used in relation to an administration line or a syringe of a powered fluid injector, the term "axial" refers to a direction along a longitudinal axis of a syringe or an administration line extending between the proximal and distal ends.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings and described in the following specification are simply exemplary aspects of the disclosure. Hence, specific dimensions and other physical characteristics related to the examples disclosed herein are not to be considered as limiting.

Figure 2A:
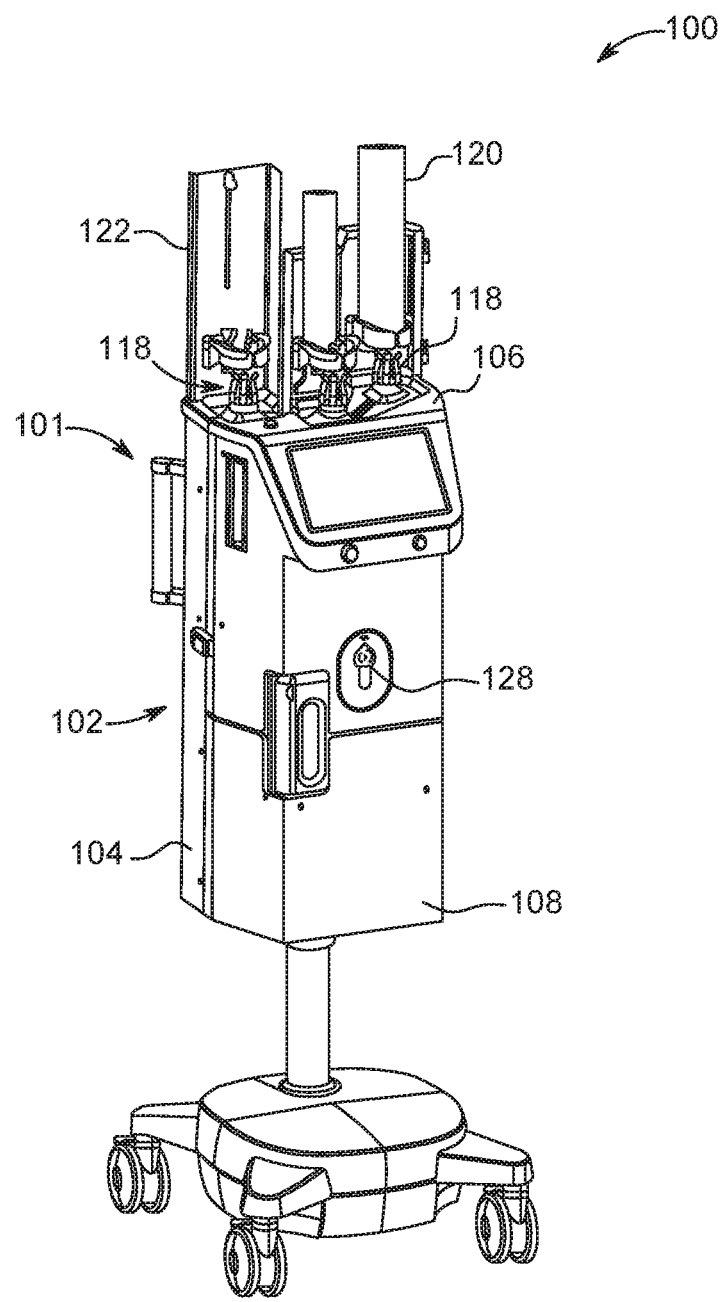
FIG. 2A is a perspective view of a powered fluid injector system in accordance with further examples or aspects of the present disclosure.
Figure 2B:
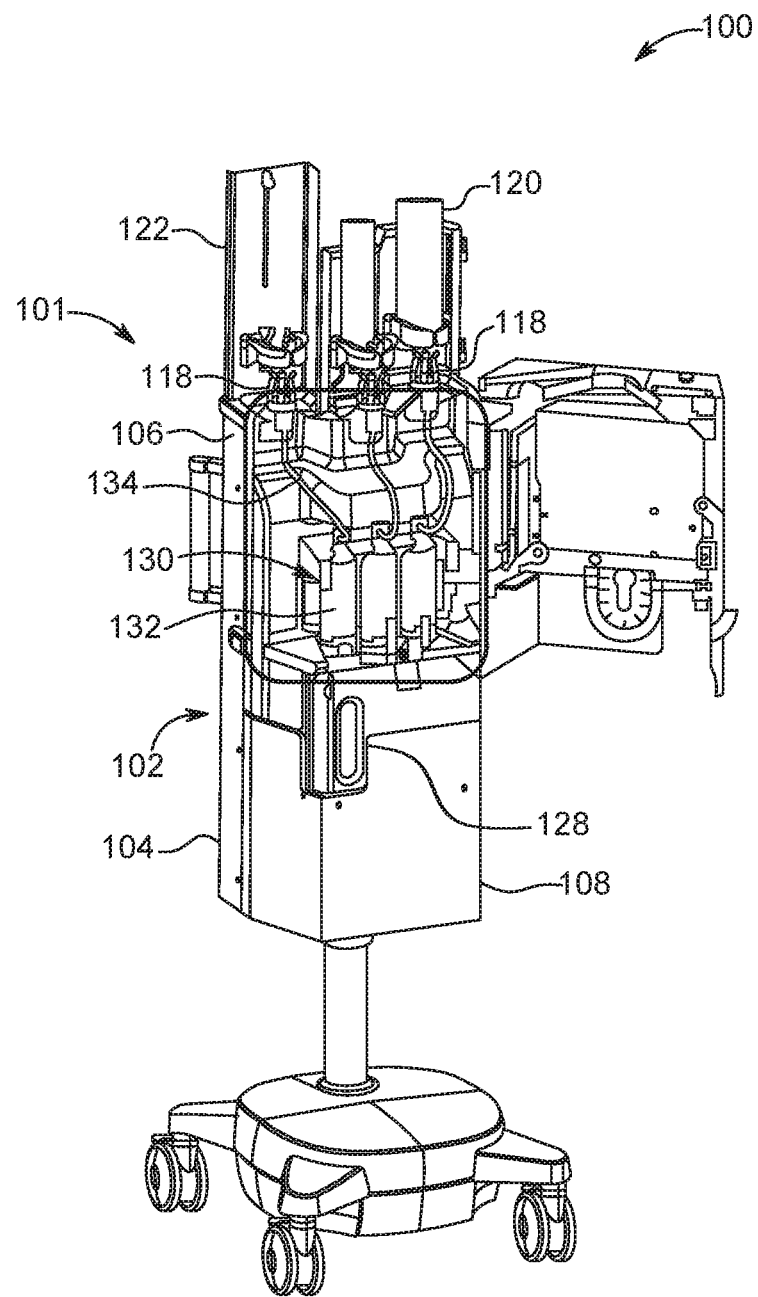
FIG. 2B is a perspective view of the powered fluid injector system of FIG. 2A with an access panel in an open position.
Figure 3:
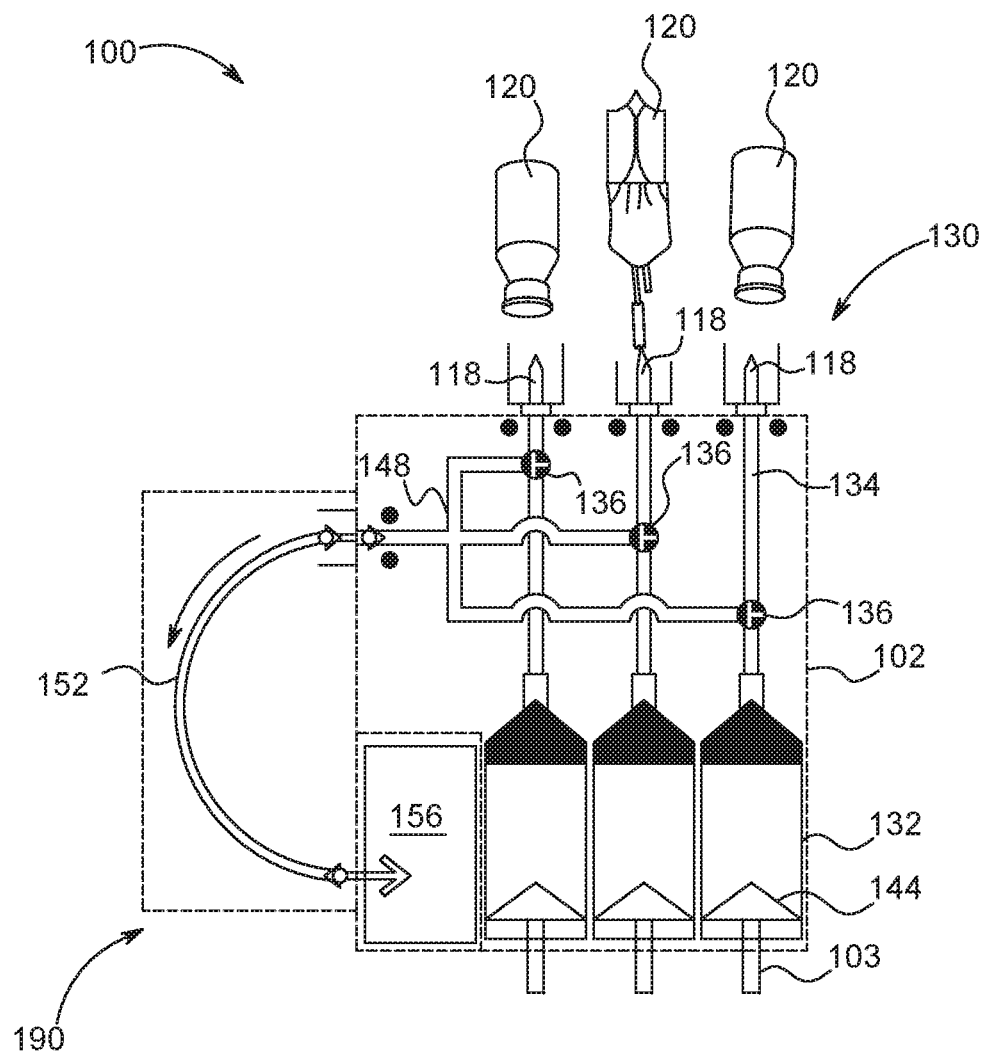
FIG. 3 is a schematic view of various fluid paths within the powered fluid injector system of FIG. 2A.

A fluid injector system 100 for providing feedback to a user about compliance with usage instructions and hygiene practices for disposables or disposable components of the system 100 is shown in FIG. 1-3. Although the present disclosure is described primarily in the context of the MEDRAD® Centargo CT Injection System, it will/should be apparent to persons of ordinary skill in the art that the present invention can be applied to a variety of injection systems inclusive of their associated disposables (e.g., syringes, tubing, etc.). Examples of such injection systems include the MEDRAD® Stellant FLEX CT Injection System, the MEDRAD® MRXperion MR Injection System and the MEDRAD® Mark 7 Arterion Injection System offered by Bayer HealthCare LLC. While the injector systems described herein primarily include both multi-use disposable components and single-use disposable components, the visual feedback and compliance summaries disclosed herein can also be used for injectors that include only single-use disposable components.

Especially with injector systems intended for multi-patient use, it is important to use disposables according to their labeling and instructions for use. In particular, some disposable components, such as the MUDS, are used by multiple patients and may have an in-use time (e.g., 4 hours, 12 hours, or daily) or maximum number of patients, after which the disposable component should be replaced. Other disposable components, such as a single-use disposable set (SUDS) or patient line, are only used on one patient and should be replaced prior to each injection.

In some examples, the fluid injector system 100 disclosed herein provides feedback about whether disposable components, such as the SUDS and MUDS, are used according to the instructions for use. Keeping track of which components are single use or multi-use and of when multi-use components should be replaced can be difficult even for facilities that want to use disposable components on-label (e.g., according to provided usage instructions). For example, when users of fluid injector systems 100, such as medical technologists, are working simultaneously or across shift changes, mistakes about when multi-use components should be replaced can occur. Further, some risk-tolerant facilities may be less strict about following usage guidelines and, accordingly, may be less exact in documenting when components should be replaced. In that case, a lack of tracking can provide a false sense of security, allowing the users to believe that they are following usage guidelines more closely than may actually be the case.

Manual or automated monitoring of fluid injector systems 100 to assess compliance with usage instructions can be difficult. For example, injector systems 100 can provide notifications to users asking the users to comply with usage instructions for disposables by replacing the MUDS and SUDS at appropriate times. However, many injector systems 100 do not have any way to monitor if the user actually complies with the notifications. Further, while some injector systems 100 produce limited log files about injections performed by the injector system 100, such log files are generally only available to service technicians. The log files often are not accessible to or regularly reviewed by users of the fluid injector systems, meaning that the users do not review the log files to determine a level of compliance. Some disposables can include barcodes, QR codes, RFID tags, or breakable components to encourage or ensure compliance with usage instructions. However, these features require additional effort by users to implement, can add complexity to manufacturing of disposable components, and/or can make disposables more fragile. Accordingly, such precautions often are not implemented. Also, in order to be truly effective, such precautions would need to render the injector device inoperable until the disposable components are removed and replaced. However, causing an injector device to become inoperable could be unsafe if, for example, there was an emergency requiring immediate medical imaging.

Rather than using such precautions that can render the fluid injector system unusable until a component is replaced, the present inventors have recognized that providing feedback to users about past compliance with usage instructions over a period of time (e.g., days, weeks, or months) may help users to appreciate how closely usage instructions have been followed and may encourage future compliance. For example, the fluid injector system 100 disclosed herein can be configured to provide a visual display 220 (shown in FIGS. 4 and 5) including indicators showing a level of compliance over discrete intervals (e.g., days, weeks, or months), making it clear to users when the disposables have been used correctly according to the labeling and when components have been used past expiration or re-used inappropriately.

Providing visual feedback about past compliance can be referred to as "retrospective monitoring." For some users, "retrospective monitoring" can be an inducement to use the disposables on-label without impacting a facility's day-to-day workflow (e.g., requiring additional actions by users to respond to notifications) or cost (e.g., requiring the facility to buy more expensive disposables that prevent reuse). Further, such retrospective monitoring can allow different departments at a facility (e.g., the radiology, hygiene, and infection control departments) to monitor utilization and visualize either proper (e.g., on-label) use or improper (e.g., off-label) use.

In order to provide such retrospective monitoring or feedback, in some examples, instead of simply displaying overall values, such as a total in-use time for a MUDS, the feedback can show a number of injections performed by improper use of the disposables. For example, as discussed herein, the visual display 220 can show a number of injection protocols performed after a MUDS has expired or a number of injection protocols performed with re-used SUDS. Focusing on a number of incorrectly performed injection protocols may make consequences of off-label use clearer for users, practitioners, and facility departments.

In some examples, providing feedback as retrospective monitoring, rather than requiring compliance with usage instructions, allows facilities to maintain a degree of control over operating decisions for their fluid injector systems 100. For example, the fluid injector systems 100 and visual feedback systems disclosed herein can be configured to provide tools for user's to monitor workflow practices, while still providing some flexibility to users regarding compliance with usage instructions. Such flexibility may be needed, for example, when a 24 hour use life limit, if strictly enforced, would negatively impact a patient. For example, in an emergency room setting, if a patient arrives near to expiration of the usable life of the component (e.g., at 23:59), delaying the treatment would have more negative consequence than allowing use of the system (briefly) past the 24 hour limit.

Generally, the fluid injector systems 100 disclosed herein provide a visual summary of compliance with use instructions. In some examples, the visual summary can be a hygiene or compliance summary or report including visual indicators showing compliance over a number of preceding intervals or days. Such a summary or report can be a useful tool for improving compliance practices without negatively impacting patient outcomes.

The fluid injector system 100 and visual feedback disclosed herein are mainly provided to help facilities use disposables safely. Additionally, in the case of an incident with the injector (e.g., patient infection), a facility could use a generated hygiene summary or report to prove that the facility regularly uses the disposables on-label. In some circumstances, an injector manufacturer could also use the hygiene or compliance summary or report to remind/re-train users on the importance of using the disposables correctly. In some instances, in the case of repeated over-use of the disposables by a particular facility, the injector manufacturer could void the warranty for fluid injector systems owned by the facility.

Fluid Injector System

Various fluid injector systems can be arranged to provide feedback about user compliance with usage instructions within the scope of the present disclosure. In some examples, as discussed herein, the feedback, visual summary, or compliance report is provided on a display, such as a control room display, of the fluid injector system. In other examples, the visual feedback is provided on a separate remote device, such as a portable computer, used by individuals at other department of the facility.

FIG. 1 shows a schematic drawing of an exemplary fluid injector system 100 having at least one reservoir, such as a syringe 132, in fluid connection with a fluid path set. The fluid path set can be the single-use disposable set (SUDS) 190, as described in detail herein. The at least one syringe 132 can be configured to be filled with at least one fluid F, such as contrast media, saline solution, or any desired medical fluid. The at least one fluid F from the at least one syringe 132 can be delivered to a patient using the SUDS 190. The at least one syringe 132 may be pre-filled or it may have the ability to be filled with the at least one fluid. The at least one syringe 132 may be, for example, a rolling diaphragm syringe, bottle, or collapsible bag.

The system 100 further includes a fluid injector 101, such as an automated or powered fluid injector, that is configured to deliver the fluid F from the syringe 132 to a patient. For example, the injector 101 may be configured to drive a plunger 144 of the at least one reservoir 132 with a drive member 103, such as a piston, to deliver the fluid F from the at least one fluid reservoir 132 via the fluid path set 190. The at least one drive member 103 may be reciprocally operable to selectively fill the at least one syringe 132 or deliver fluid from the at least one syringe 132. In some examples or aspects, the injector 101 may be configured to releasably receive the syringe 132. The injector 101 may be a multi-syringe injector, wherein several syringes may be oriented side-by-side or in another spatial relationship and are separately actuated by respective pistons associated with the injector 101.

Fluid flow from the at least one syringe 132 may be regulated by a fluid control module or controller 123 that is configured to operates various valves, stopcocks, and flow regulating structures to regulate the delivery of the at least one fluid F to the patient based on user selected injection parameters, such as injection flow rate, duration, and total injection volume.

In some examples, the controller 123 can have one or more buttons, knobs, touch pads, displays, switches, dials, or other input and/or output devices to allow the user to user to manually select the injection parameters, or select a pre-defined injection protocol. Alternatively, this functionality may reside with an external control unit or with the fluid injector system 100. In either case, the controller 123 controls, for example but not limited to, the injection pressure, the volumes and flow rates of the various fluids to be delivered to the patient, and/or the ratio of the various fluids to be delivered to the patient.

In addition to operating the injector 101 to provide an injection of fluid to the patient, the controller 123 or, as described in detail herein, another controller or processor connected to or in wired or wireless communication with the controller 123, can be configured to provide feedback regarding compliance with usage instructions. For example, the controller 123 or another controller or processor of the system 100 can be configured to cause a visual display 220 (shown in FIGS. 4 and 5) to display various indicators related to compliance or non-compliance with usage instructions. The controller 123 can also be configured to track data related to compliance and, in some examples, to update the stored data following each injection protocol. As discussed previously, an "injection protocol" can be a protocol comprising one or more injections to be performed for a patient. Each injection can comprise one or more phases according to which the desired fluid(s) can be administered to the patient so as to effect enhancement of at least one region of interest in a patient's body over the scan duration of a diagnostic imaging procedure.

Another exemplary fluid injector system 100 which can be adapted to provide feedback about compliance with usage instructions is shown in FIGS. 2A and 2B. Unlike in the previous example, the syringes 132 are positioned in the injector 101, as shown in FIG. 2B. The exemplary fluid injector system 100 includes the powered fluid injector 101 connected to a fluid delivery set intended to be associated with the injector device 101 to deliver fluids from one or more single-dose or multi-dose containers and fluid path sets under pressure into a patient. The fluid injector 101 includes an injector housing 102 with opposed lateral sides 104, a distal or upper end 106, and a proximal or lower end 108. The housing 102 encloses the various mechanical drive components, electrical and power components necessary to drive the mechanical drive components, and control components, such as electronic memory and electronic control devices (hereinafter electronic control device(s)), used to control operation of reciprocally movable drive members, such as drive members 103 (shown in FIGS. 1 and 3) associated with the fluid injector system 100. Such drive members 103 may be reciprocally operable via electro-mechanical drive components, such as a ball screw shaft driven by a motor, a voice coil actuator, a rack-and-pinion gear drive, a linear motor, and the like.

The fluid injector system 100 can further includes at least one bulk fluid connector 118 for connection with at least one bulk fluid source 120. Alternatively, the fluid source could be a single dose vial, rather than a bulk source. In some examples or aspects, a plurality of bulk fluid connectors 118 may be provided. For example, as shown in FIGS. 2A and 2B, three bulk fluid connectors 118 may be provided in a side-by-side or other arrangement. In some examples or aspects, the at least one bulk fluid connector 118 may be a spike configured for removably connecting to the at least one bulk fluid source 120, such as a vial, bottle, or a bag. The at least one bulk fluid connector 118 may have a reusable or non-reusable interface with each new bulk fluid source 120. The at least one bulk fluid connector 118 may be formed on or attached by tubing with the multi-patient disposable set, as described herein. The at least one bulk fluid source 120 may be configured for receiving a medical fluid, such as saline, an imaging contrast solution, or other medical fluid, for delivery to the fluid injector system 100. The housing 102 may have at least one support member 122 for supporting the at least one bulk fluid source 120 once it is connected to the fluid injector system 100.

With reference to FIG. 2B, the fluid injector system 100 may further include the disposable components for conveying the fluid to the patient. For example, the system 100 can include the multi-use disposable set or MUDS 130 positioned inside the housing 102. Examples and features of the MUDS are described in detail in International Application No. WO 2016/112163, entitled "Multiple Fluid Delivery System with Multi-Use Disposable Set and Features Thereof," the disclosure of which is incorporated herein by reference in its entirety.

In some examples, the MUDS 130 can include one or more syringes or pumps 132 connected to and/or in fluid communication with the bulk fluid source(s) 120 through a MUDS fluid path 134. In some examples, the number of syringes 132 may correspond to the number of bulk fluid sources 120. For example, the MUDS 130 can include three syringes 132 in a side-by-side arrangement such that each syringe 132 is fluidly connectable to one or more of the bulk fluid sources 120. In some examples, one or two bulk fluid sources 120 may be connected to one or more syringes 132 of the MUDS 130.

The MUDS 130 can be removably connected within the housing 102 of the fluid injector system 100 for delivering one or more fluids from the one or more bulk fluid sources 120 to the patient. As described in further detail herein, the system 100 can also include sensors for identifying when the MUDS 130 is connoted to and/or removed from the system 100.

The MUDS 130 may be configured for delivering fluid to a fluid path set, such as the SUDS 190, as described herein. In order to establish fluid communication between the MUDS 130 and the SUDS 190, the fluid injector system 100 can further include at least one slot or connection port 128 for releasably connecting the single-use connector or disposable set (e.g., the SUDS 190) to the MUDS 130.

The SUDS 190 can include, for example, a connector configured to be received by the connection port 128. The connection port 128 can include sensors for identifying when the SUDS 190 is connected to the port 128. The SUDS 190 can further include a patient line for conveying fluid from the MUDS 130 to the patient. Exemplary SUDS 190 are described in International Application Publication No. WO 2015/106107, entitled "Single-use disposable set connector," which is incorporated by reference herein in its entirety.

FIG. 3 shows a schematic drawing of components of the MUDS 130 enclosed within a housing 102 of the fluid injector system 100. As shown in FIG. 3, a syringe plunger 144 is disposed within each syringe 132 and is reciprocally movable within the syringe 132 due to movement of a drive member 103 associated with the fluid injector system 100. Each syringe 132 is in fluid communication with a valve 136 which provides fluid communication with a manifold 148 and bulk fluid connector 118. The manifold 148 may also provide support for the syringes 132 so that the syringes 132 can be handled as a single, unitary structure. The manifold 148 may be in fluid communication via the valves 136 and/or the syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120.

In some examples, when not connected to the patient's catheter (e.g., prior to fluid injection), a patient line 152 of the SUDS 190 can be connected to a waste reservoir 156 on the fluid injector system 100. The waste reservoir 156 is desirably separate from the syringes 132 to prevent contamination. In some examples, the waste reservoir 156 is configured to receive waste fluid expelled from the syringes 132 during, for example, a priming operation. The waste reservoir 156 may be removable from the housing 102 in order to dispose of the contents of the waste reservoir 156. In other examples, the waste reservoir 156 may have a draining port (not shown) for emptying the contents of the waste reservoir 156 without removing the waste reservoir 156 from the housing 102. In some examples, the waste reservoir 156 is provided as a separate component from the MUDS 130.

Fluid Injector System Environment

Figure 4:
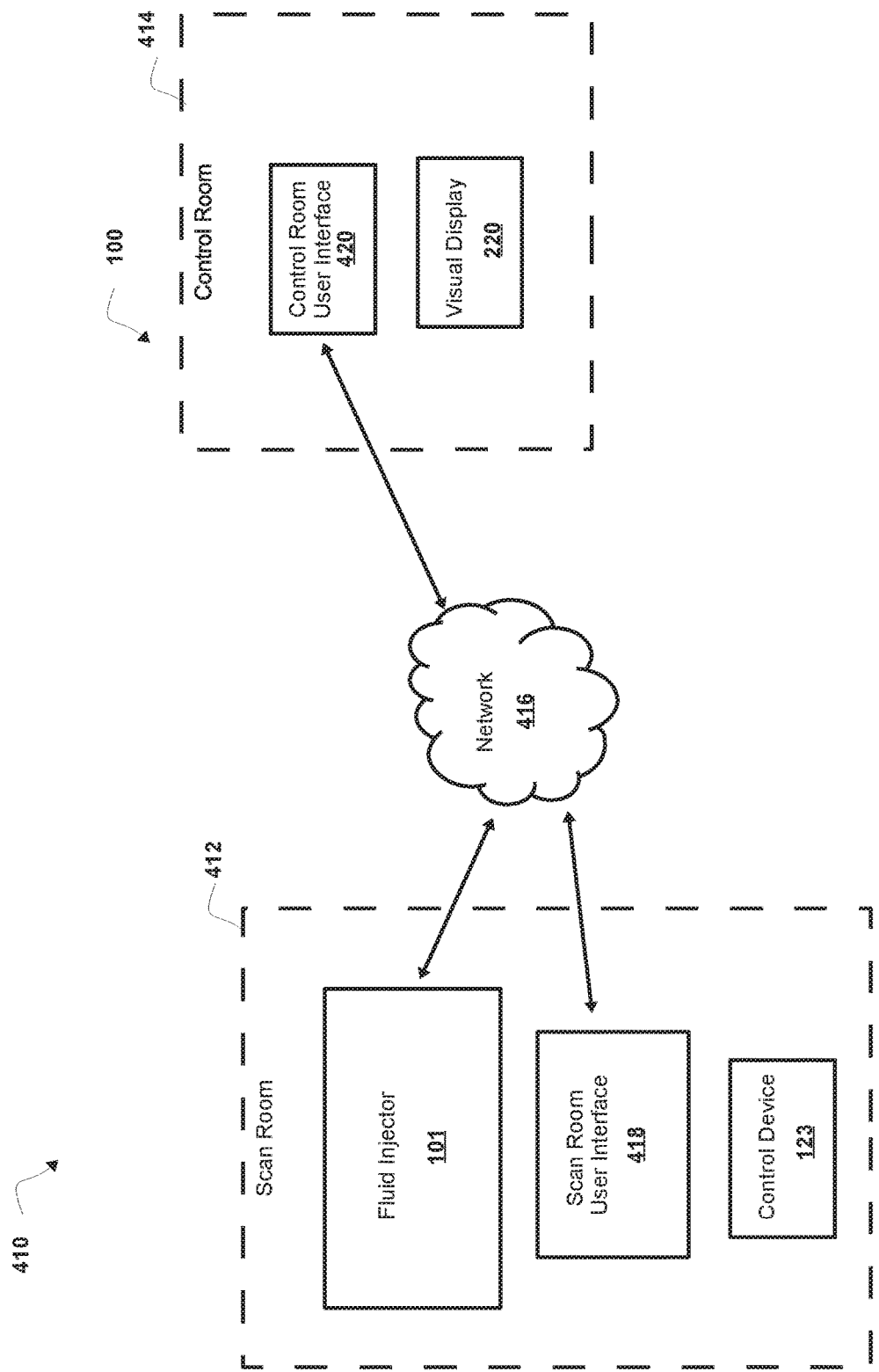
FIG. 4 is a schematic drawing of an environment of use for a fluid injector system including a scan room and a control room, in accordance with some examples or aspects of the present disclosure.

With reference to FIG. 4, the fluid injector system 100 can be configured to be used in an environment 410 including a scan room 412 and a control room 414. For example, the fluid injector system 100 can be a bifurcated system in which some functions, processing, and control operations are performed by devices located in the scan room 412 and other functions, processes, and control operations are performed by devices, processors, and displays located in the control room 414. The devices in the different rooms 412, 414 can communicate via a wired or wireless computer network 416.

As shown in FIG. 4, the fluid injector 101 and associated control device 123 are located in the scan room 412. The control device 123 can be configured to provide a scan room user interface 418 for controlling the injector 101 from the scan room 412. The scan room user interface 418 can be located on the fluid injector 101 and, for example, can include a display or touch screen display and associated buttons on the injector housing 102 for operating the injector 101. A user, such as a medical technologist, can set injection parameters and perform other actions to prepare an injection protocol using the scan room user interface 418. The scan room user interface 418 can also provide feedback to the user, such as feedback informing the user when the injector 101 is primed and ready to begin performing an injection protocol.

Some processes for generating the visual compliance summary are performed by controllers and processors in the scan room 412. For example, the control device 123 of the injector 101 can be configured to identify when a disposable component is inserted into the injector 101 based on signals detected by sensors of the fluid injector 101. The control device 123 may also record a time when a disposable component is inserted into or removed from the injector 101. The control device 123 could also be configured to record a time that an injection protocol is started or completed.

The control room 414 can be a shielded control room outside the scan room 412. From the control room 414, the user, such as the medical technologist, can monitor the fluid injector system 100 during an injection protocol in a safe and convenient location. The control room 414 can include a computer device, such as a computer terminal, including one or more controllers or processors for controlling operations of the system 100 and fluid injector 101 from the control room 414. The computer devices or terminal in the control room 414 can provide a control room user interface 420 that allows the user to input instructions to the system 100 and injector 101 and to receive feedback from the system 100. Feedback can include information about a progress of an injection protocol and, for example, a confirmation when an injection protocol is complete. The feedback can be provided on the visual display 220 in the control room 414.

Some processes related to the generation and display of the visual compliance summary are performed by the computer device or terminal in the control room 414. For example, the computer terminal in the control room 414 may be configured to receive information about the disposable component(s) from the fluid injector 101 and generate the visual compliance summary or report based on the received information. Once generated, the visual compliance summary or report could be displayed to a user on the visual display 220 in the control room 414. In some examples, the user can use the control room user interface 420 to customize portions of the component report by, for example, manipulating the reports or selecting different portions of the report to review. For example, as described in further detail herein, the user can toggle through compliance summaries for different periods of time or time intervals using the user interface 420. The user may also control how compliance information is displayed. For example, using the control room user interface 420, the user may select which information is displayed (e.g., only SUDS, only MUDS, or both). The user may also control an appearance of certain visual indicators shown on the visual display 220. For example, the user could control which types of graphs or numerical values are included in the compliance report or summary.

In some examples, the compliance report or summary could be generated by a controller or processor in the control room 414. Once generated, the summary or report could be made available users at a remote location. For example, the compliance summary or report could be accessed remotely over the computer network 416. For example, remote users could review the compliance summary or report using a personal portable computer devices, such as a tablet or laptop.

Electrical Devices of Fluid Injector Systems

Figure 5:
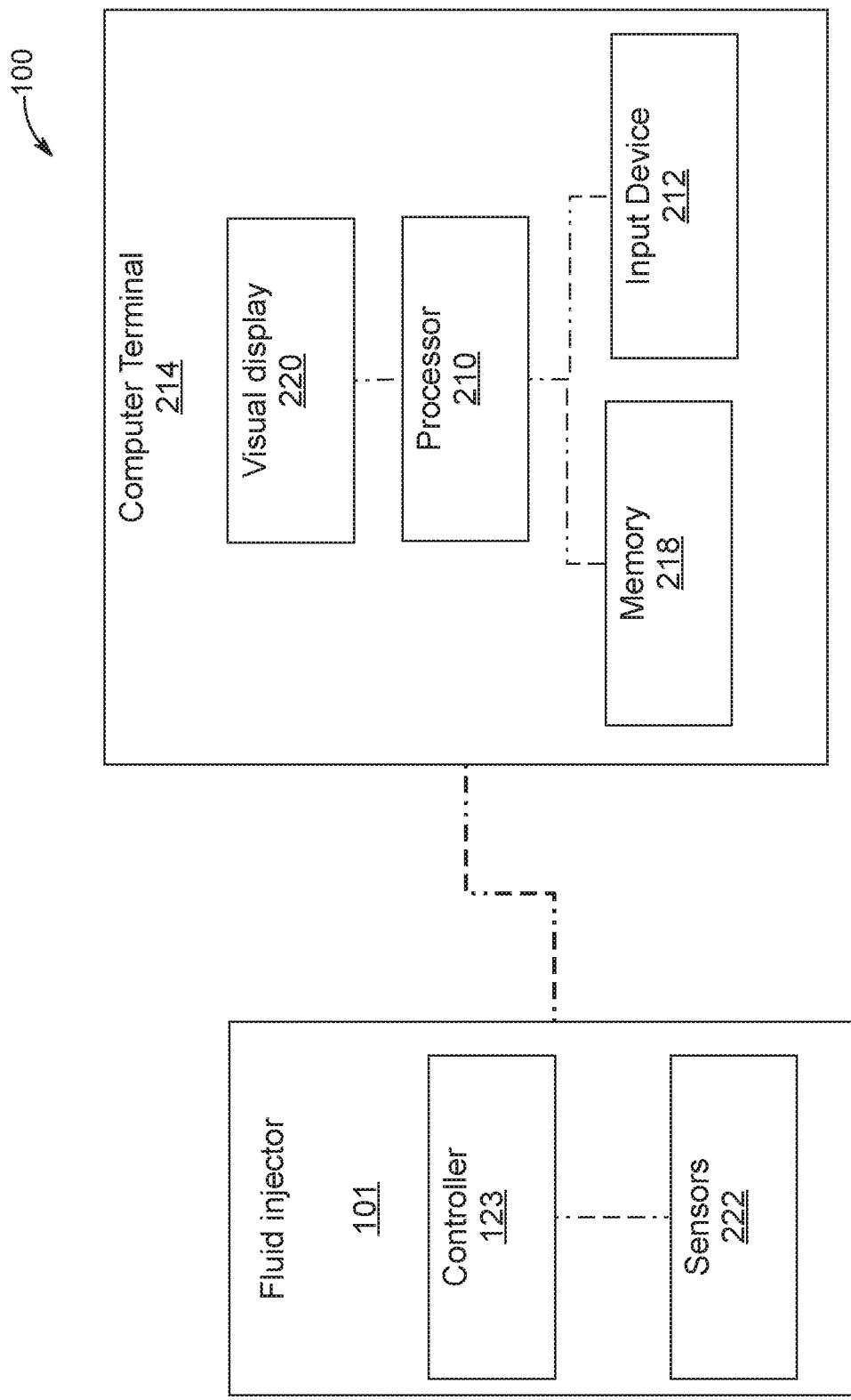
FIG. 5 is a schematic drawing showing electronic components of a fluid injector system in accordance with some examples or aspects of the present disclosure.

With reference to FIG. 5, electrical components of the fluid injector system 100 are shown and described in detail. As discussed previously, some electrical components and processing circuitry can be located in the scan room 412. Other electrical components and processing circuitry of the system 100 can be located in or can be accessed from the control room 414.

In some examples, the system 100 includes at least one control device, such as a computer processor 210, for generating the compliance report or summary and displaying the report to a user. In some examples, the control device or processor 210 is a processor of the controller 123 (shown in FIG. 1) of the fluid injector 101 located in the scan room 412. In that case, the processor 210 and associated controller 123 could generate the visual compliance summary or report and transmit the summary or report to a remote device for viewing by a user. In other examples, as shown in FIG. 5, the control device or processor 210 can be a separate processing component remote from and in communication with the controller 123 of the injector 101. For example, the processor 210 could be a component of a control terminal 214 located in the control room 414 or at another location remote from the injector 101. The computer terminal 214 can be configured to control the fluid injector system 100. In other examples, the processor 210 could be a component of a general computer device, such as a computer tablet, smart phone, or laptop computer in communication with and configured to receive information from the controller 123 of the injector 101.

As shown in FIG. 5, the control terminal 214 can includes the processor 210, the visual display 220, system memory 218 for storing information about the injector protocols, and one or more input devices 212 for entering information about the injection protocols being performed and/or for reviewing the generated compliance summaries or reports. As will be discussed in further detail hereinafter, the at least one processor 210 of the system 100 is configured to receive or determine information about an injection protocol performed by the injector system 100. For example, the information can include a time that an injection is performed. The processor 210 can also receive information about when a disposable component was connected to the injector 101. Such information could be determined, for example, based on signals detected by sensors 222 associated with the injector system 100. For example, certain sensors 222 could be positioned to determine when the MUDS 130 is inserted into the injector housing 102. The same or different sensors 222 could be used to determine when the SUDS 190 is connected to the injector 101 through the injector port 128 and/or when the SUDS 190 is in fluid communication with the MUDS 130. The sensors 222 could be optical, proximity, and/or pressure sensors positioned on the fluid injector 101 to detect insertion and removal of the sets 130, 190. The fluid injector controller 123 and/or processor 210 can be configured to receive signals from the sensors 222. Based on the received signal, the controller 123 and/or processor 210 can be configured to identify, for example, a time that the disposable set was connected to the injector 101.

As described in detail herein, the processor 210 can be configured to process and analyze the received information to determine a status of the disposable component(s) for each injection protocol. Based on the analysis of the received information, the processor 210 can also be configured to record compliance information in the system memory 218, thereby creating a record of compliance over a period of time. The processor 210 also generates the visual summary of compliance based on stored information, and provides the visual summary to the visual display 220 so that it can be displayed to users. It is noted that users receiving the visual summary can include a variety of individuals depending on work flow practices and needs of particular facilities. For example, the visual compliance summary could be displayed to the medical technologist performing an injection protocol to remind the user about the importance of complying with usage instructions. The visual summary could also be reviewed by, for example, a team of medical technologists at the end of a day, week, or month to evaluate levels of compliance with usage instructions. For example, all technologists who perform injections at a particular facility may review the visual summary once a week to evaluate how the team collectively complies with usage instructions for replacing disposable components.

Methods for Generating Compliance Summaries

Figure 6:
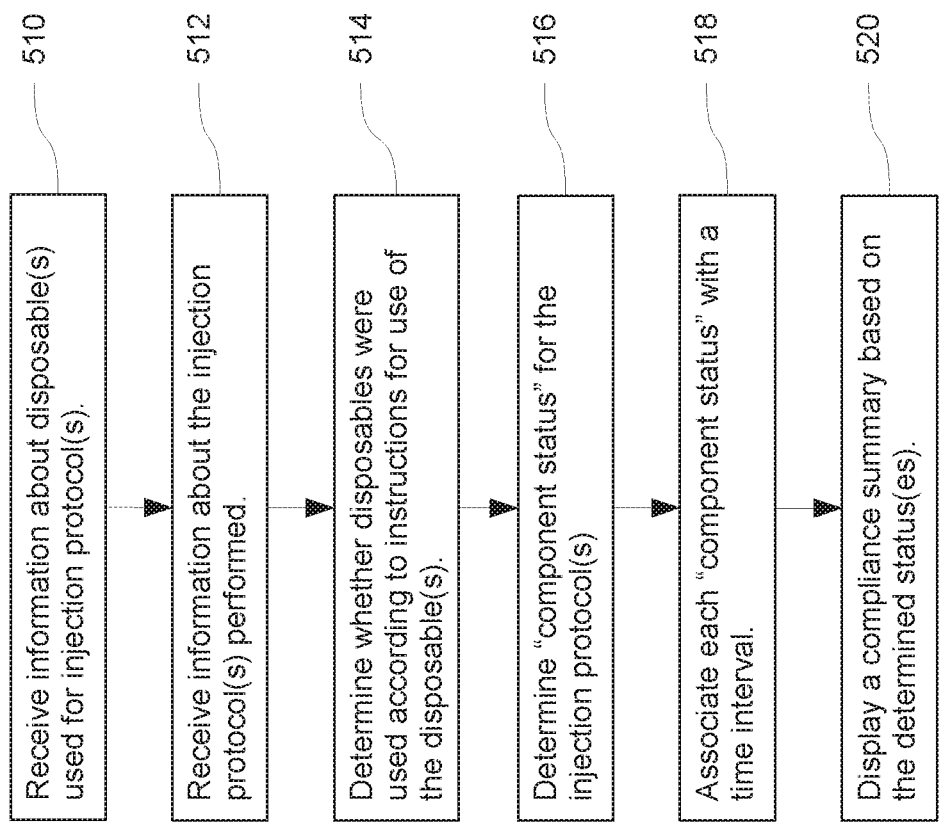
FIG. 6 is a flow chart showing steps for monitoring compliance with usage instructions and generating a visual summary of compliance for a fluid injector system, in accordance with some examples or aspects of the present disclosure.
Figure 7A:
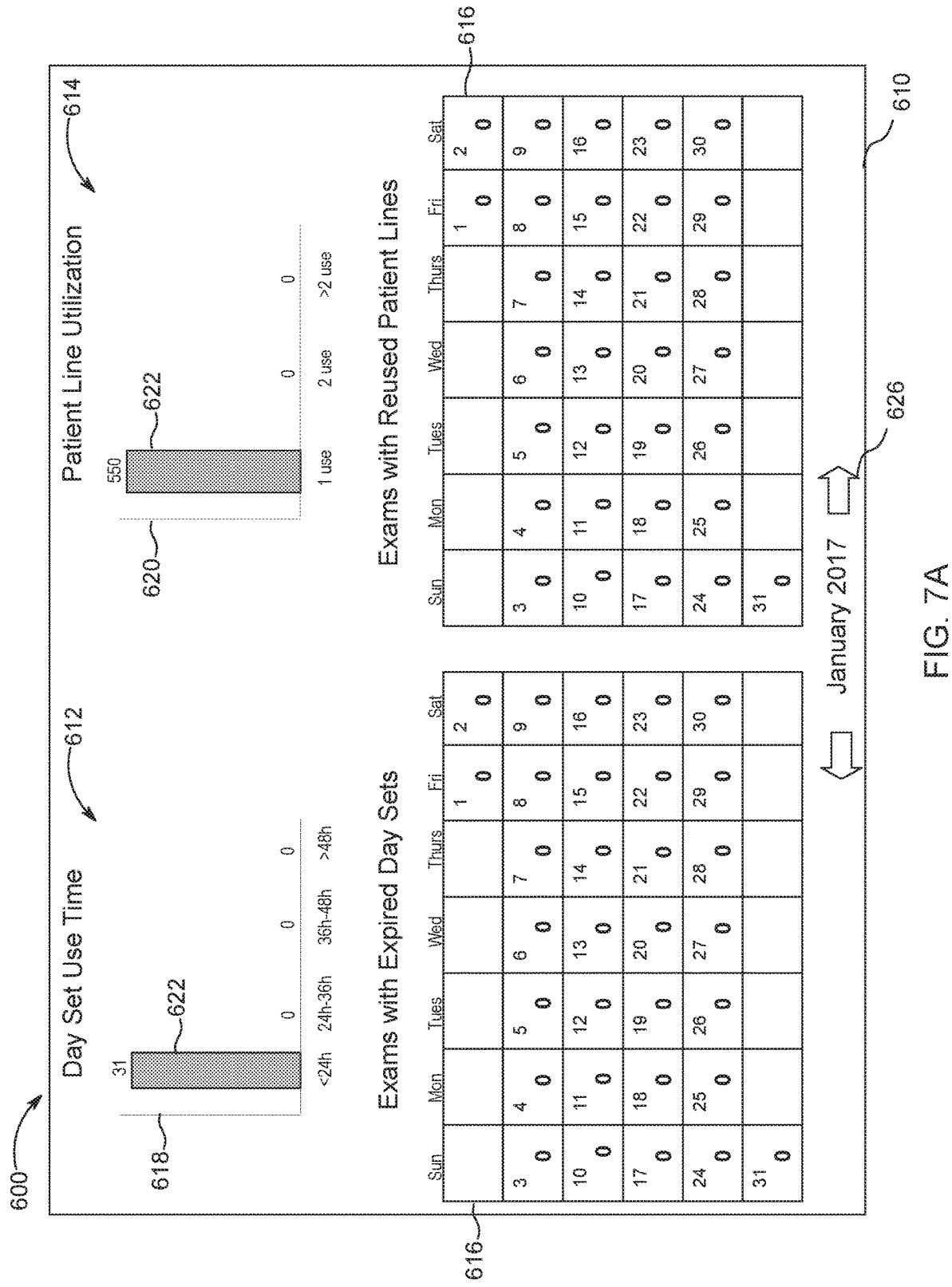
FIG. 7A is a screen capture of a visual summary of compliance with usage instructions showing good compliance, in accordance with some examples or aspects of the present disclosure.
Figure 7B:
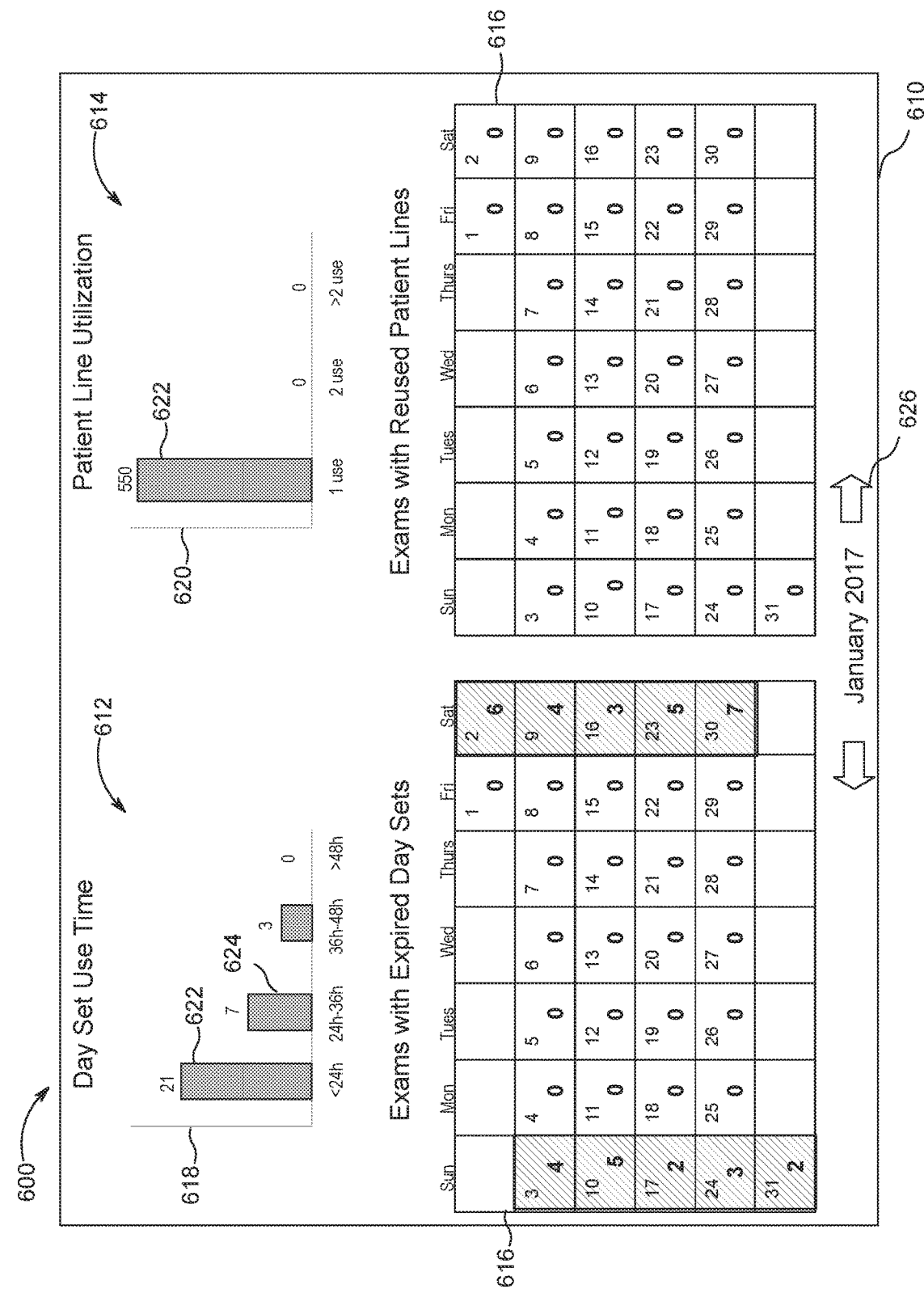
FIG. 7B is a screen capture of a visual summary of compliance with usage instructions showing partial compliance, in accordance with some examples or aspects of the present disclosure.
Figure 7C:
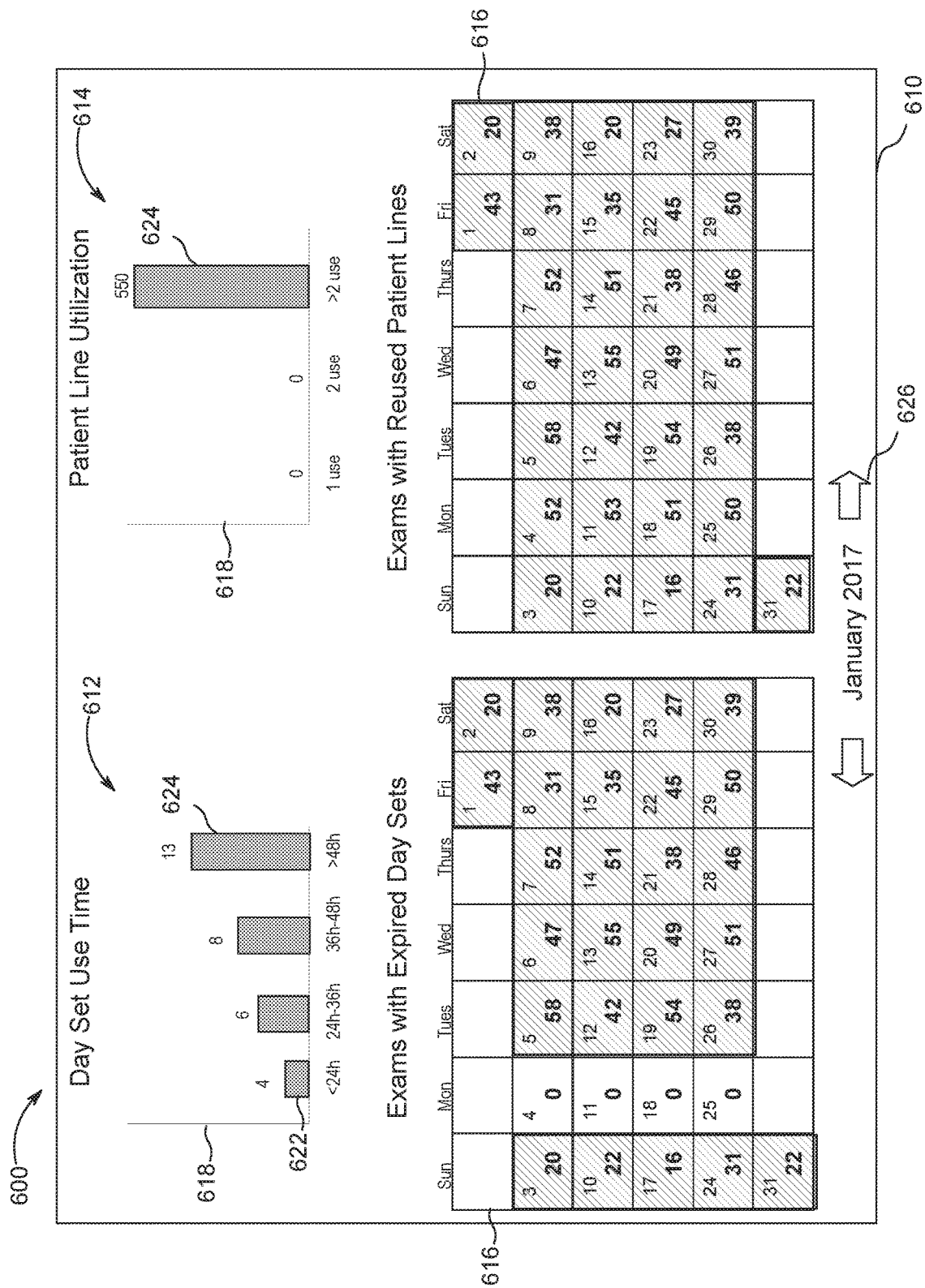
FIG. 7C is a screen capture of a visual summary of compliance with usage instructions showing poor compliance, in accordance with some examples or aspects of the present disclosure.

Having described features of the fluid injector system 100 and visual display 220, steps performed by the processor 210 for generating and displaying the visual compliance summary or report will now be discussed in detail. A flow chart showing steps performed by the processor to generate the compliance summary or report is shown in FIG. 6. Screen captures showing examples of visual summaries that can be generated according to the method and displayed to users are shown in FIGS. 7A-7C.

At step 510, the at least one processor can be configured to receive information about the at least one disposable component used during an injection protocol. In some examples, the processor receives information about two disposable components (e.g., both the SUDS and the MUDS). For the MUDS, the received information can include a time (e.g., an "installation time") when the MUDS was installed to the fluid injector. As discussed previously, the installation time can be determined from sensors on the fluid injector that detect when the disposable component is connected to the injector. Based on the installation time, an "end use time" can be calculated. For example, for the MUDS, the end use time can be 4, hours, 12 hours or 24 hours after the installation time. For MUDS which are configured to be used by a predetermined number of patients or for a predetermined number of injection protocols, the information provided to the processor can include information about how many injection protocols have been performed since the MUDS was installed to the fluid injector system.

For a single-use disposable set or SUDS, a new set or patient line should be installed prior to each injection protocol. In that case, the information received by the processor can be a confirmation that a new SUDS was installed prior to the injection protocol being performed. The confirmation can be based on information received from the sensors on the fluid injector. If sensors on the fluid injector did not detect that a new SUDS was installed prior to beginning the injection protocol, the processor could receive an indication that use of the SUDS did not follow the instructions for use of the SUDS.

At step 512, the at least one processor can also be configured to receive information about an injection protocol performed by the system 100 or that is being performed by the system 100. For example, the information can include a date and time, referred to herein as an "occurrence time" for the injection protocol. The occurrence time can be recorded during each injection protocol and stored on system memory along with the information about the disposable component being used for the injection.

At step 514, the processor is configured to determine whether disposable components used for an injection protocol complied with the usage instructions for the disposable components. For example, the processor can be configured to compare the "occurrence time" for an injection protocol to an "end-use time" for the MUDS to determine whether the MUDS was used past its end-use or expiration time. Also, the processor could determine whether a new SUDS was installed for the injection protocol.

At step 516, based on the determination of whether the use of the disposable component(s) complied with the instructions for use, the processor can be configured to determine a "component status" for each of the disposable components used for the injection protocol. For example, the component status can include a first status indicating whether the MUDS was past its expiration or end-use time when the injection protocol was performed. The processor can also provide a second status for the single-use component or SUDS. The component status could indicate, for example, whether the single use component or SUDS was new and only used for a single patient.

As used herein, the "component status" is an indication of whether use of the component complied with or did not comply with the instructions for use for the disposable component. For example, the stored information could be a simple "yes" or "no" for each component and for each injection protocol performed by the injector. The "component status" could also include information about a degree or level of compliance or non-compliance. For example, the "component status" could include how many hours past expiration the MUDS was being used. For the SUDS, a level of non-compliance could include recording how many injection protocols were performed using the same SUDS. The "component status" can be stored in a spreadsheet, database, or lookup table located on system memory, so that the information can be easily accessed when generating the visual summary. The processor can be configured to update the spreadsheet, database, or lookup table each time that additional information is received by the processor.

At step 518, the processor is configured to associate each received component status with a time interval of a plurality of time intervals. The time intervals can be a predetermined period over which compliance is monitored, such as each shift, daily, or weekly. As discussed previously, the processor can be configured to record a time and date of each injection protocol. In that case, the time and date information can be used to associate each received component status with the appropriate time interval. As discussed herein, the visual summary can show compliance over each time interval rather than only providing a total compliance rate or ratio for a longer period of time. It is believed that by showing compliance over shorter time periods or intervals, users will better appreciate how closely they are complying with usage instructions and, in some cases, the effects of failure to comply for individual patients or on specific days.

At step 520, the processor is configured to cause the visual display to display the compliance summary or report. The compliance summary or report can include, for example, at least one visual indicator for each time interval. The visual indicator for each time interval provides visual feedback to a user regarding whether the received at least one component status for a particular interval shows that use was in compliance with the usage instructions for the at least one disposable component. For example, the visual indicator may have a first appearance if all received component statuses for a particular interval showed usage in compliance with usage instructions. The visual indicator may have a second appearance if some or all use within a particular interval did not comply with usage instructions. In some examples, the visual summary includes one visual indicator for each time interval. As discussed previously, showing the user feedback for multiple intervals on a single screen or summary may help the user to evaluate how the facility uses disposables on a daily, weekly, and monthly basis. For example, the user may see which days or weeks had good compliance and which days or weeks did not. In this way, the user is provided with an accessible and easy to review summary, which is believed to encourage improved compliance.

In some examples, the visual compliance summary can include different sections for each disposable component of the injector system. For example, the visual summary could include a first section including visual indicators showing whether use of the multi-use component or MUDS complied with usage instructions. The visual summary could also include a second section showing visual indicators for whether use of the single-use component or SUDS complied with usage instructions.

In some examples, the visual compliance summary is a matrix including a space for the visual indicator for each time interval. For example, the matrix can be a weekly, monthly, or yearly calendar including a space for each 24 hour period. In this way, as shown in the screen captures 600 of FIGS. 7A-7C, the user is provided, in a single screen, with a visual summary of compliance for each day. By reviewing the visual summary, the user can easily recognize, for example, a number of days with poor compliance or days of the week where compliance is low. In some examples, the visual summary can also include indicators of a total compliance over a plurality of intervals, such as an entire week or month. The total compliance can be based, for example, on information for each component status received by the system over the plurality of time intervals. In some examples, total compliance can be shown as a visual indicator of compliance similar to the visual indicators for each interval. For example, the total compliance indicator could be a shape having a first appearance if compliance is good, a second appearance if compliance is fair, and a third appearance when compliance is poor.

Alternatively or in addition, total compliance can be provided with numeric representations on the visual summary. For example, total compliance could be shown as a ratio or percentage of injection events that complied with usage instructions compared to a total number of injection events performed. A total compliance ratio or percentage could be provided for both the multi-use component or MUDS and the single use component or SUDS. In other examples, total compliance could be shown as a bar graph or histogram including a first bar indicating compliance and a second bar indicating non-compliance. The bar graphs could also include multiple bars showing, for example, a level of non-compliance or whether non-compliant uses were close to compliance with the usage instructions or far from compliance. For example, using a MUDS within 3 to 6 hours of its expiration time is closer to compliance with the usage instructions than is using the MUDS 48 hours past its expiration time.

Visual Summaries of user Compliance

With reference to FIGS. 7A-7C, screen captures 600 from the visual display showing the visual summary of compliance with usage instructions are shown. As shown in FIGS. 7A-7C, the visual summary 610 includes a first section 612 including feedback for the multi-use component or MUDS and a second section 614 including feedback for the single use component or SUDS. Each section 612, 614 includes the calendar 616 including a space for each day of a month (e.g., January 2017). Each day can be color coded or can include another visual indicator to show whether use during that day complied with usage instructions. As used herein, use in compliance with usage instructions can mean, for the MUDS, that the MUDS was replaced at the beginning of the day and that no injections were performed using a MUDS past its expiration date. For the single-use component or SUDS, use in compliance with usage instructions can mean that the SUDS was replaced prior to each injection and that no injection was performed during the day using a SUDS which had already been used for a previous patient. In addition to the color coding or visual indicator, numerical values showing, for example, a number of out of compliance injections performed per day or a ratio of compliant vs. non-compliant injections can also displayed in the spaces of the calendar 616.

In some examples, as shown in FIGS. 7A-7C, the summary 610 also includes one or more bar graphs 618, 620 showing a total amount of compliance for all time intervals (e.g., for each day of a week or month). For example, the summary 610 can include a bar graph 618 for the MUDS or daily set showing how long the MUDS had been in-use when an injection was performed for each injection performed over the month. The bar graph 618 includes a first bar 622 showing the number of "compliant" injections, meaning that the MUDS had been in use for less than 24 hours. The bar graph 618 also includes non-compliant bars 624 showing injections performed past the MUDS expiration date (e.g., 24 h-36 h, 36 h-48 h, or >48 h) from when the MUDS was installed.

The summary 610 can also include a bar graph 620 for the single-use component or SUDS showing, for example, how many patients each single-use component or SUDS was used for. The bar graph 620 includes a compliant bar 622 showing the number of SUDS used during the month, which were used for only one patient. The graph 620 also includes one or more non-compliant bars 624 showing a number of SUDS used for more than one (e.g., 2 or >2) patient.

In some examples, the screen capture 600 displays compliance information for a limited period of time (e.g., a week or a month). However, compliance information for other time periods may also be available and could be reviewed by users if needed. For example, as shown in FIGS. 7A-7C, the screen 600 displays compliance information for one month (January 2017). A user can toggle to other months using the arrows 626 displayed on the screen 600.

FIGS. 7A-7C show visual summaries 610 for facilities with different levels of compliance with usage instructions. For example, FIG. 7A is a screen capture 600 showing a visual summary 610 with proper or good compliance. As shown in FIG. 7A, all of the spaces in the calendar 618 show that the injections performed that day followed usage instructions. The bar graphs 618, 620 also show that all injections were in compliance with usage instructions. This compliance summary 610 indicates that the facility always replaced the single-use connector or SUDS for each new patient. Also, the multi-use connector or MUDS was replaced every 24 hours, such that no injection was performed using a multi-use connector or MUDS that had been in use for more than 24 hours.

FIG. 7B shows a partially compliant facility, in which there is proper or good compliance most days of the month. However, as shown in FIG. 7B, the facility is not in compliance on Saturdays and Sundays for the multi-use component or MUDS. Instead, as shown in FIG. 7B, the facility uses the multi-use connector installed on Friday all day Saturday and Sunday. For example, the facility may decide that since an injector is only used infrequently on weekends, it is not worth the cost to replace the MUDS on Saturday or Sunday. The bar graph 618 also shows that some injections were performed using MUDS that had been in use for 24 hours to 48 hours. As shown in FIG. 7B, the facility is fully compliant in replacing the single-use component or SUDS for each new patient.

FIG. 7C shows a facility with improper or poor compliance. For example, as shown in the calendar 618 in FIG. 7C, the facility changes its multi-use set or MUDS once a week (on Mondays). The same multi-use set or MUDS is used all week. Thus, as shown in the bar graph 618, many injections are performed using a MUDS that has bene in use for 24 hours to 48 hours, or longer. Also, the facility routinely uses the single-use component or SUDS on more than one patient. In fact, as shown in the bar graph 620 every SUDS used over the month was used for more than two patients. Accordingly, the calendar 618 for the patient line or SUDS in FIG. 6C shows that the facility was not compliant each day of the month.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:

1. A fluid injector system for use in administering to a patient at least one fluid in an injection protocol in connection with a diagnostic imaging procedure, the fluid injector system including at least one display, the fluid injector system comprising:
  a control device operably associated with at least one drive component for use in pressurizing the at least one fluid through at least one disposable component into a patient; and
  the control device including at least one processor programmed or configured to enable programming of an injection protocol comprising one or more injections, each of the injections comprising one or more phases according to which the at least one drive component pressurizes the least one fluid through the at least one disposable component into the patient so as to effect enhancement of at least one region of interest thereof over a scan duration of the diagnostic imaging procedure;
  wherein the control device is further programmed or configured to:
    determine, for each of the injection protocols performed by the fluid injector system, a component status for the at least one disposable component wherein the component status indicates whether use of the at least one disposable component was compliant with instructions for use applicable to the at least one disposable component; and
    enable the at least one display to display a compliance report, the compliance report comprising one or more visual indicators providing visual feedback about compliance with the instructions for use based on the component status determined for each of the injection protocols performed using the fluid injector system; and
  wherein the control device is further programmed or configured to at least one of:
    (a) determine (i) an occurrence time for each of the injection protocols and (ii) for each of the injection protocols, an installation time for the at least one disposable component used for the injection protocol; and
    (b) for each of the injection protocols performed by the fluid injector system, associate the component status determined for the at least one disposable component with a time interval of a plurality of time intervals;
  wherein, for each of the injection protocols, the determination of the component status is based on a comparison between the installation time for the at least one disposable component and the occurrence time for the injection protocol.

2. The fluid injector system of claim 1, wherein the component status indicates whether the use of the at least one disposable component of the fluid injector system was compliant with the instructions for use applicable thereto or was not compliant with the instructions for use applicable thereto.

3. The fluid injector system of claim 1, wherein the component status indicates that use of the at least one disposable component was compliant with instructions for use applicable thereto when the occurrence time for the injection protocols is within a predetermined period from the installation time of the at least one disposable component.

4. The fluid injector system of claim 1, further comprising at least one sensor configured to detect installation of the at least one disposable component into the fluid injector system.

5. The fluid injector system of claim 4, wherein the control device is further programmed or configured to determine the installation time of the at least one disposable component into the fluid injector system based on information received from the at least one sensor.

6. The fluid injector system of claim 1, wherein the at least one disposable component comprises at least one of a multi-use component of the fluid injector system or a single-use component of the fluid injector system.

7. The fluid injector system of claim 1, wherein the component status for each injection protocol comprises a first status for a multi-use component of the fluid injector system and a second status for a single-use component of the fluid injector system.

8. The fluid injector system of claim 7, wherein the multi-use component comprises at least one syringe configured to be used by multiple patients, and wherein the single-use component comprises a patient line configured to be placed in fluid communication with the at one syringe and used by a single patient.

9. The fluid injector system of claim 8, wherein the instructions for use applicable to the multi-use component permit the multi-use component to be used for at least one of a predetermined period of time or a predetermined number of injection protocols.

10. The fluid injector system of claim 1, wherein the compliance report comprises at least one of the one or more visual indicators for each time interval of the plurality of time intervals, the at least one visual indicator for each time interval being based on the component status determined for the at least one disposable component associated with the time interval of the plurality of time intervals.

11. The fluid injector system of claim 10, wherein the compliance report comprises a matrix comprising a space for each of the at least one of the one or more visual indicators for each time interval of the plurality of time intervals.

12. The fluid injector system of claim 10, wherein the at least one of the one or more visual indicators for each time interval of the plurality of intervals comprises a first appearance when each component status for the time interval indicates compliance with the instructions for use, and a second appearance when at least one of the component statuses for the interval indicates that use was not compliant with the instructions for use of the at least one disposable component.

13. The fluid injector system of claim 10, wherein the compliance report further comprises at least one visual indicator for total compliance generated based on the determined component statuses for each of the plurality of time intervals.

14. The fluid injector system of claim 13, wherein the visual indicator for total compliance comprises a bar graph comprising a first bar indicating compliance and at least one second bar indicating non-compliance.

* * * * *

UNITED STATES PATENT AND TRADEMARK OFFICE
CERTIFICATE OF CORRECTION

PATENT NO. : 12,168,112 B2
APPLICATION NO. : 17/044192
DATED : December 17, 2024
INVENTOR(S) : Kemper et al.

Page 1 of 1

It is certified that error appears in the above-identified patent and that said Letters Patent is hereby corrected as shown below:

In the Specification

In Column 3, Line 8, delete "brake" and insert -- break --, therefor.

In Column 3, Line 38, delete "the least" and insert -- the at least --, therefor.

In Column 4, Line 45, delete "the least" and insert -- the at least --, therefor.

In Column 13, Line 29, delete "connoted" and insert -- connected --, therefor.

In the Claims

In Column 21, Line 13, in Claim 1, delete "the least" and insert -- the at least --, therefor.

Signed and Sealed this
Eighteenth Day of February, 2025

Coke Morgan Stewart
*Acting Director of the United States Patent and Trademark Office*